United States Patent [19]

Packko et al.

[11] 4,237,172

[45] Dec. 2, 1980

[54] SEALING LEAKS BY POLYMERIZATION OF VOLATILIZED AMINOSILANE MONOMERS

[75] Inventors: Joseph J. Packo, 2504 Pebble Beach Dr., Austin, Tex. 78747; Donald L. Bailey, Traverse City, Mich.

[73] Assignee: Joseph J. Packo, Austin, Tex.

[21] Appl. No.: 966,327

[22] Filed: Dec. 4, 1978

[51] Int. Cl.³ ............................................. B32B 35/00
[52] U.S. Cl. ....................................... 428/63; 106/33; 405/264; 106/287.11; 427/140; 427/142; 138/97; 427/237; 427/248 A; 156/94; 427/248 B; 427/248 R; 166/294; 528/28; 166/295; 252/374; N; 264/36
[58] Field of Search ............... 106/33, 287.11; 138/97, 138/98; 156/94; 166/294, 295; 252/374; 260/448.2 N, 448.8 R; 264/36; 405/264; 427/140, 142, 248 A, 248 B, 248 R, 237; 428/63; 528/28

[56] References Cited

U.S. PATENT DOCUMENTS

| | | |
|---|---|---|
| 2,259,875 | 10/1941 | Bent et al. ........................ 166/294 X |
| 2,265,962 | 12/1941 | Bent et al. ............................... 166/22 |
| 2,566,363 | 9/1951 | Pedlow et al. ..................... 260/448.8 |
| 2,570,719 | 10/1951 | Rudel et al. .......................... 252/49.6 |
| 2,579,418 | 12/1951 | Cheronis ................................... 260/2 |
| 2,624,721 | 1/1953 | Hatcher et al. ....................... 260/46.5 |
| 2,635,059 | 4/1953 | Cheronis . |
| 2,876,209 | 3/1959 | de Benneville et al. ............. 260/45.4 |
| 2,876,234 | 3/1959 | Hurwitz et al. .................... 260/326.5 |
| 3,007,886 | 11/1961 | Parker ..................................... 260/18 |
| 3,036,019 | 5/1962 | Molotsky et al. ......................... 260/2 |
| 3,043,798 | 7/1962 | Boyer et al. .......................... 260/46.5 |
| 3,054,818 | 9/1962 | Pepe et al. .......................... 260/448.8 |
| 3,098,830 | 7/1963 | Rochow .................................... 260/2 |
| 3,133,108 | 5/1964 | Finestone .......................... 260/448.2 |
| 3,133,110 | 5/1964 | Morehouse et al. .............. 260/448.2 |
| 3,187,030 | 6/1965 | Boyer et al.. ................. 106/287.11 X |
| 3,305,525 | 2/1967 | Goosens .............................. 260/46.5 |
| 3,361,547 | 1/1968 | Packo ...................................... 48/193 |
| 3,467,686 | 9/1969 | Creamer ............................ 260/448.2 |
| 3,483,735 | 12/1969 | Packo ..................................... 73/40.7 |
| 3,483,736 | 12/1969 | Anderson .............................. 73/40.7 |
| 3,507,725 | 4/1970 | Hylak ...................................... 156/94 |
| 3,523,771 | 8/1970 | Anderson ............................... 48/193 |
| 3,530,092 | 9/1970 | Borchert ............................. 260/46.5 |
| 3,572,085 | 3/1971 | Packo ..................................... 73/40.5 |
| 3,578,479 | 5/1971 | Packo ................................. 138/97 X |
| 3,578,490 | 5/1971 | Bauer et al. |
| 3,580,939 | 5/1971 | Cerzeriat et al. ............. 260/448.2 N |
| 3,608,000 | 9/1971 | Anderson ............................... 264/36 |
| 3,634,560 | 1/1972 | Anderson ............................... 264/36 |
| 3,660,984 | 5/1972 | Anderson .......................... 61/36 R |
| 3,709,712 | 1/1973 | Rossman ........................... 138/97 X |
| 3,711,305 | 1/1973 | Anderson ............................... 106/33 |
| 3,711,309 | 1/1973 | Packo ................................ 264/36 X |
| 3,716,384 | 2/1973 | Anderson ............................... 106/33 |
| 3,923,736 | 12/1975 | Nitzsche et al. ............... 260/46.5 G |
| 4,026,976 | 5/1977 | Anderson ............................... 264/36 |
| 4,074,536 | 2/1978 | Young .............................. 166/295 X |

*Primary Examiner*—John T. Goolkasian
*Assistant Examiner*—Robert A. Dawson
*Attorney, Agent, or Firm*—Browdy and Neimark

[57] ABSTRACT

Leaks in a vessel or pipeline or the like adapted for containing a fluid, are sealed by means of a volatilized polymerizable aminosilane supplied to the interior of the vessel under sufficient pressure and for a sufficient period of time to permit contact thereof and react in the presence of moisture or sand at the situs of the leak to provide a solid polysiloxane seal.

14 Claims, No Drawings

SEALING LEAKS BY POLYMERIZATION OF VOLATILIZED AMINOSILANE MONOMERS

FIELD OF THE INVENTION

The present invention relates to sealing leaks in pipes, conduits, closed containers, tanks, and closed systems adapted to contain or transport fluids. The invention is particularly adapted for sealing leaks in buried pipes used for conveying fuel gas and also for sealing leaks in telephone conduits containing nitrogen or other inert gas under pressure.

BACKGROUND OF THE INVENTION

In an article entitled "Detection, Repair, and Prevention of Gas Leaks," published in the American Gas Journal, August 1959, pages 16–28, it is indicated that the amount of fuel gas lost from pipelines through leakage represents a great economic burden as well as a potential safety hazard. In addition, leakage of fuel gas reduces the effective capacity of a gas distribution system. Another adverse effect of leakage is a reduction in the level of pressure in the distribution mains below desirable limits.

In U.S. Pat. No. 3,507,725 to Hylak et al. there is disclosed a method of repairing gas main fibrous packed joints with a liquid sealing material which may be a liquid monomer such as styrene monomer, by introducing the monomer into the gas main in liquid form, and permitting it to flow to a low point in the system where a leaking joint exists, the packing of which becomes saturated with the sealant which then polymerizes over a relatively long period of time, namely six weeks to three months. Styrene is employed as a liquid, and no specific catalyst is named in the patent.

My U.S. Pat. No. 3,578,479 discloses sealing leaks in a vessel and the like with a sealant agent which is either a silicon hydride, a boron hydride or an alkoxide borane, together with a metal alkyl. To achieve success, this system requires the use of the metal alkyl, a dangerously pyrophoric material, as a co-reactant. Moreover, such metal alkyl have a poor shelf life and are easily subject to contamination. The seal produced by the co-reaction has a tendency to be brittle and lacks consistency and homogeneity due to stratifications which inevitably occur in the mixtures and differences in volatility curves in the components which give different relative concentrations at different temperatures.

Likewise, U.S. Pat. No. 3,608,000 to Anderson discloses the introduction into a vessel of sealants which are mixtures of volatile organosilanes and metal alkyls which react chemically to form solid products in accordance with the equations set forth at column 2, lines 4–5 of the patent. These systems, again requiring the same metal alkyl co-reactants as required in U.S. Pat. No. 3,578,479, suffer the same disadvantages.

Bent et al. U.S. Pat. No. 2,265,962 discuss in general the use of silanes for sealing wells by reaction of the silane with water to form an insoluble shield or plug. Among the silanes mentioned are those containing nitrogen groups including the following four compounds: $Si(NH_2)(OC_2H_5)_3$; $Si(NH_2)(OCH_3)_3$; $Si(NO_2)(OC_2H_5)_3$; $Si(OC_2H_4NH_2)_4$. These compounds are either too unstable or too low in volatility to be practical for use in gas phase sealing.

The Ceyzeriat U.S. Pat. No. 3,580,939 discloses the use of amino-silanes as cross-linking agents for diorgano-polysiloxane compositions. These liquid compositions, which harden spontaneously in the presence of water, are suggested for joining slabs and pipes.

Anderson U.S. Pat. No. 4,026,976 shows the sealing of pipe leaks using a catalytically polymerizable volatile organic monomer, but this process undesirably requires the use of a catalyst which consequently complicates the processing and increases the cost.

In addition to the Anderson patents mentioned above, a number of other prior patents show the use of volatile mixtures for pipe sealing. These include the Anderson U.S. Pat. Nos. 3,634,560; 3,711,305; 3,716,384; Packo U.S. Pat. No. 3,483,735; and Anderson U.S. Pat. No. 3,660,984. Also of interest in this regard is the Rossman U.S. Pat. No. 3,709,712 which relates to the use of volatile organic amines; and Packo U.S. Pat. No. 3,711,309 which relates to the use of volatile alcohol or glycol ethers. Of somewhat less interest are the patents to Anderson U.S. Pat. Nos. 3,483,736; 3,523,771; Packo 3,572,085; and 3,361,547, which relate to the detection of gas leaks.

In spite of all the work which has been done in the field of gas phase sealing, as noted above, most sealing of gas containing pipe continues to be carried out by archaically attempting to locate the leak, then excavating at the believed site of the leak, followed by applying a physical patch to the leak. Dogs are still being trained to sniff out gas leaks, although flame ionization is often used; these are both expensive techniques, and very often are unable to pinpoint the leak site, as gas may leak from one point and travel along the pipe for a considerable distance before reaching the surface where it can be detected. Also excavation is not only expensive but is impractical in some cases as where gas lines pass beneath large buildings.

Significant sealing problems also continue to occur in other gas containing conduits as well. Both above-ground and underground telephone conduits cannot tolerate moisture, as moisture tends to impregnate the dielectric material separating the telephone wires with the result that cross-talk occurs between adjacent lines; this problem is presently controlled at great expense by constantly feeding dry gas, e.g. nitrogen under pressure through the telephone conduit. Problems of gas leakage also occur in many other environments including chemical processing plants and air conditioning units.

SUMMARY OF THE INVENTION

It is, accordingly, an object of the invention to overcome deficiencies in the prior art, such as indicated above.

It is another object of the present invention to provide for the improved sealing of leaks in pipes, pipelines, conduits, tubing and vessels using a gaseous aminosilane or a mixture of gaseous aminosilanes.

It is another object to provide for an improved process for sealing leaks in pressurized pipes, pipelines and vessels which provide a better seal, which is safer, and which uses materials which are more stable and non-pyrophoric.

It is a further object to provide improved pipe seals which are more flexible and less brittle and therefore less likely to fail in the event of movement of the pipe, e.g. in the event of earth shifts, and which seal is more homogeneous.

It is yet a further object to provide for improved vessel sealing using a volatile, volatilizable or gaseous sealing compound which has good shelf life and is not easily contaminated.

It is yet another object of the present invention to provide for a volatile, volatilized or gaseous sealing material which may be used by itself and without the presence of a gaseous metal compound.

In accordance with the instant invention there is provided a novel process for sealing leaks in pipes, pipelines and pipe systems, conduits, closed containers, tanks, and closed systems such as air conditioner units adapted to contain gaseous fluids, all of which are referred to generally as a vessel. The process of the invention is particularly adapted for sealing leaks in underground piping systems used for conveying fuel gas, as well as for sealing leaks in telephone conduits containing nitrogen or other inert gas under pressure, air conditioner units containing Freon and other gaseous systems such as chemical plants and refrigeration units.

The invention not only eliminates leakage of gas into the atmosphere, but also into the surrounding soil or through joint packing materials. The air and the other surrounding materials which may be involved in the sealing operation are accordingly referred to herein as the ambient environment.

The sealing method of the present invention is particularly adapted for the sealing of leaks in piping systems employing joints of the type sealed by fibrous packings, but it is not to be regarded as limited thereto. Fibrous packed joints are extensively employed in city gas distribution systems in which cast iron pipe sections are connected by bell-and-spigot type joints caulked with fibrous packing, usually jute fiber. However, the method of the invention may also be employed for sealing small hole-type leaks, such as those caused by corrosion, in the body of the pipe sections. The seal so produced, because of its electrical insulating characteristics, also tends to retard further corrosion induced by electrical effects.

According to the invention, the sealant precursor is introduced into the interior of the vessel under pressure in gaseous form or in volatile liquid form, where it volatilizes within the vessel, at preferably ambient temperature. When the sealant compound begins to escape through any existing leak in the vessel, it reacts with soil or moisture present at the ambient exterior locus of the vessel where the leak exists and polymerizes to form a solid product in situ which seals the leak.

DETAILED DESCRIPTION OF THE INVENTION

The present invention employs the novel principle of sealing a leak in a vessel or pipeline or the like by introducing into the interior of the vessel in vapor form a normally gaseous or volatilizable or volatilized organosilane monomer which is capable of polymerizing in contact with materials in the environment such as moisture, soil or sand or a combination of these agents. Polymerization is effected at the situs of the leak where in contact with the polymerization inducing material, the monomer forms a solid polymeric product which acts as a seal.

Where desirable, the pipeline or vessel may be first flushed with an inert gas, before the monomer is introduced. The vapors of the organic monomer are preferably introduced in admixture with a gaseous vehicle or carrier which is inert to the monomer. The inert gaseous vehicle or the flushing gas may be, for example, nitrogen, helium, natural gas, or, in the case of air conditioning units, the Freon itself.

The concentration of monomer vapor employed will depend upon the type of monomer, the type of sealing problem present, the nature and size of the leaks, the environmental conditions of the vessel or pipeline, particularly the moisture level and the pressure and temperature of the carrier gas in the vessel, and the like. In general, the concentration of monomer will be on the order of about 100 to 50,000 parts per million, preferably 2,500 to 25,000 parts per million, but this is to be considered as illustrative, and not as limiting.

The polymerization reaction may take place within a relatively short time, usually a matter of a few hours.

Thus, in accordance with one aspect of the practice of the invention, illustrated by the polymerization system in Example 1 below, the aminosilane is introduced into the vessel, in vapor form, or volatilizable liquid form so as to reach the points in vapor form where leakage may be taking place. In the case of an underground pipeline or gas main, the leakage may be taking place at jute packed joints, or at corrosion sites, into the surrounding soil. In such cases a matrix of either jute or soil is available to absorb the aminosilane vapors, providing a site for the polymerization to take place. The monomer is introduced into the vessel under a pressure sufficient to permit escape of its vapors from the leak into the ambient environment.

Sealing may be effected either statically or dynamically. Under static sealing methods, the part of the vessel (e.g. a gas line) to be sealed is isolated from the remainder of the vessel, and such part is then purged of its contents by displacement with carrier gas under pressure and containing the aminosilane vapor, it being understood that the carrier gas may be any gas inert to the aminosilane, e.g. natural or fuel gas where the vessel is a gas line. Under appropriate conditions, pre-flushing or pre-moisturizing may be first carried out. After feeding of the carrier gas aminosilane mixture, the infeed end of the vessel is closed, and the gas is permitted to leak from the leak holes, after which the vessel is tested for tightness. Static sealing may be repeated a plurality of times until the vessel is fully sealed. Static sealing may be faster and therefore preferred when the vessel is relatively small, e.g. a short length of pipeline.

However, dynamic sealing is usually preferred. This may be carried out by feeding the aminosilane monomer continuously or intermittently into the vessel with the usual component carried by the vessel, e.g. natural or fuel gas as the carrier in the case of gas pipelines, or nitrogen as the carrier in the case of telephone conduits. Such feeding may be carried out in the same manner in which odorants are conventionally admixed with natural or fuel gas, e.g. by wicking, spraying or atomizing, or merely pumping the monomer in liquid form into the vessel where it then vaporizes with the flow of carrier gas. In such dynamic sealing, carrier gas with aminosilane vapor continues to leak through each leak hole until it becomes sealed.

In many cases polymerization will take place more effectively after the aminosilane monomer has stopped flowing at the leak site, i.e. either static sealing or intermittent dynamic sealing. Therefore when dynamic sealing is called for, it may be desirable to add the aminosilane intermittently, or alternatively with moisturized carrier gas. Intermittent feeding may also be desirable from an economic viewpoint.

In any vent, the aminosilane is supplied either continuously or for a period of time sufficient to allow polymer formation and the establishment of a solid seal at the situs of the leak. This point is usually indicated by a build-up of pressure within the vessel to a steady level.

In the case of a small closed system, such as an automobile air conditioning unit, the aminosilane monomer may be incorporated into the original fluid material, e.g. the Freon, in which case the unit will self seal as it develops leaks.

When this system is employed to seal a pipeline, such as, for example, a gas main distribution system utilizing jute packed joints, there must be taken into consideration the mode of operation of the line. Some gas systems are used for transmission of dry natural gas, and in these the jute packing may have hardened so that it is difficult for the aminosilane to be taken up by the jute. Similarly, where the pipeline is buried in very dry environments, a similar problem may exist. In such situations, in order to ensure the presence of adequate moisture at the location of the leak into the surrounding soil, it is desirable to pretreat the line by injection of moisture to the level needed to either render the packing absorptive of moisture or the soil surrounding the leak sufficiently moist to initiate polymerization. Although most soils contain some moisture, under dry conditions it is desirable to introduce sufficient moisture into the system to assure proper polymerization conditions. However, moisture becomes less important where sufficient silica lies adjacent the leak hole.

Injection of the aminosilane may be repeated as many times as required to reach a no-leak condition, e.g. a steady internal pressure indicative of sealing of leakage where static sealing is carried out.

As noted above, the sealant aminosilane gas may be introduced intermittently, alternating with the feed of moisturized carrier gas. Where the carrier gas is natural or fuel gas, the aminosilane can be introduced simultaneously with the odorants and in a similar manner. This system is particularly useful when it is desired to treat the entire gas distribution system simultaneously, for leaks already in existence and for new leaks as they develop.

A key aspect of the present invention is the proper selection of a sealing compound. In accordance with the present invention, such a suitable material is an aminosilane which is volatile at ambient temperatures and which is polymerized by contact with moisture or soil at the situs of the leak. More particularly, the requirements of the sealant compound are as follows:

- (1) it must be an aminosilane;
- (2) it must have sufficiently high vapor pressure at ambient temperature, i.e. at 30°–90° F., and the internal vessel pressure, to give gas mixtures containing at least 100 parts per million of the sealant vapor, when mixed with the carrier gas and preferably at least 2500 parts per million of the aminosilane vapor; and
- (3) the compound must be a monomer and be capable of polymerizing from the vapor state to form a solid silicone polymer or polysiloxane in the presence of moisture or soil.

In addition, it is desirable that the volatile aminosilane monomer also be environmentally acceptable. It is further desirable that such monomer be non-corrosive and sufficiently stable so that storage presents little difficulty.

It has been found that such a material corresponds generally to the following formula, bearing in mind that the alkyl groups designated must be of relatively short chain length or else the aminosilane will not be volatile at ambient temperatures,

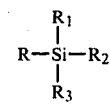

wherein R is H, halogen or R', and R' is alkyl of 1–4 carbons;

$R_1$ is halogen, R', —OR', —NHR' or —N(R')$_2$, preferably R' or —OR';

$R_2$ is halogen, R', —OR', —NHR' or —N(R')$_2$ preferably —OR' or N(R')$_2$; and $R_3$ is —NHR' or —N(R')$_2$, preferably —N(R')$_2$.

Aminosubstituted silane monomers prepared by reacting primary amines with chlorosilane monomers are included, e.g. where one or more of $R_1$ to $R_3$ is NHR'.

Examples are:

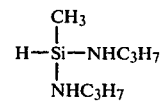

bis(isopropylamino) methylsilane

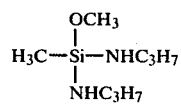

di-isopropylamino-methoxy-methylsilane

Generally, however, aminosilanes made from primary amines are less stable than those made from secondary amines, and therefore these monomers are less practical and are not preferred.

Amino-substituted silane monomers containing halogen attached to the silicon atom are also included, e.g. dimethylamino methyl chloro silane, dimethylamino dimethyl chloro silane, dimethylamino methyl dichloro silane, dimethylamino methyl difluorosilane, dimethylamino dimethyl fluorosilane, etc. However, these also are not preferred, particularly where the vessel to be sealed is of metal, because of their potential to cause corrosion problems, to say nothing of concerns regarding toxicity and environmental impact.

Mixtures of the above compounds may also be used and also mixtures of such compounds with less volatile aminosilanes, so long as the mixture is volatile at the temperature and pressure of use. In general, it is desired that the aminosilane or mixture thereof be volatile at 30° F., i.e. at least 100 parts per million and preferably 2500 parts per million in the gaseous atmosphere.

Of useful materials which fall within the general formula above, that most preferred is

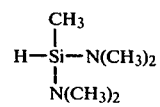

Other useful aminosilanes and mixtures thereof are as follows:

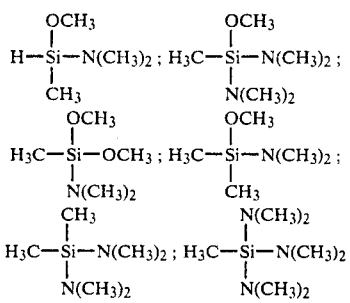

Bis-(dimethylamino)dimethylsilane in combination with tris-(dimethylamino)methylsilane, the latter being used in quantities of 1–5% of the silane blend; mixtures of the above listed aminosilanes.

The following examples further illustrate without limiting the nature of the invention.

EXAMPLE 1

Bis(dimethylamino)methylsilane was made according to the following reaction scheme:

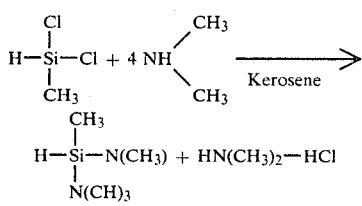

Gaseous dimethylamine was passed through one mol of MeHSiCl$_2$ in 700 ml of kerosene until the reaction was complete. The amine HCl precipitated and was removed from the liquid by filtration. The product was recovered by vacuum distillation.

EXAMPLE 2

A ½×50-inch pipe was drilled with two ⅛-inch holes, two 1/16-inch holes, and two 1/32-inch holes spread eight inches apart. It was then buried with eight inches of wet sand (15.2% H$_2$O) above and below the pipe. The pipe was then fogged by passing N$_2$ through H$_2$O and then through the pipe for one hour. This was followed by bubbling N$_2$ (cylinder pressure ~5 psi) through a container of the bis(dimethylamino)methylsilane product of Example 1 to volatilize the silane, and then through the pipe. A total of 49.0 g of the silane was used in a three-hour sealing period.

After the N$_2$ flow carrying the gaseous aminosilane was stopped, the system was allowed to stand intact for 88 hours. It was then found that the pipe would hold a pressure of 15 psi with no leaks. The sand was dropped from the bottom of the box to reveal the pipe. A small ball of polymer had developed at the site of each hole. The polymer seals had the appearance of mounds of sand and the sand had obviously been incorporated into the polymer. The polymer over one of the 1/16-inch holes was partially removed by cutting into it with a knife. It was found to be a tough, hard material.

The seal that was partially cut away was removed nearly to the original hole. The system was then pressured with nitrogen and checked for leaks with each increase of 10 psi. At 60 psi the system was leak-free, but in the presence of charging to 70 psi, the seal which had been partially cut away ruptured. This hole was sealed with a hose clamp and gasket, and the system was then pressured to 100 psi with no leaks at the remaining five seals.

EXAMPLE 3

A ½×50-inch pipe with six 1/16-inch holes spaced eight inches apart was barricaded at intervals so that one hole was buried in wet dirt (soil high in clay and containing ~20% H$_2$O), two holes were buried in dry sand (0.2% H$_2$O), two holes were buried in wet sand (~10% H$_2$O), and one hole was sealed with gasket and hose clamp.

The N$_2$ bubbling through the bis(dimethylamino)methylsilane was adjusted to 1.5 on the flow meter (~0.3 liter/minute) and flow was continued for 12 hours, using a total of 205 g of the silane. The flow was then stopped and the system allowed to stand intact for 64 hours. At the end of this time it required three seconds for the pipe to drop from a pressure of 5 to 0 psi, whereas at the beginning of the experiment the leaks in the pipe were so large that no pressure could be developed with the nitrogen regulator set at 10 psi.

EXAMPLE 4

The bell end of a three-inch bell and spigot pipe was utilized in an attempt to effect a seal around a straight section (not flared) of the pipe. The two sections of pipe were clamped together with pipe strap and the opening at the joint was packed with dry (not oiled) Oakum which had been soaked with water. There was no other sealing material, such as lead which is frequently used, utilized at the joint. When nitrogen was passed through the pipe, it was observed that there was a massive leak at the jute seal. With the nitrogen regulator set at 10 psi there was no pressure build up in the pipe.

The pipe was buried in eight inches of wet (10–12% H$_2$O) sand a flow of N$_2$ bubbled through the bis(dimethylamino)methylsilane. The flow meter was adjusted to a reading of 1.0 (0.25 liter/minute), and the N$_2$-silane mixture flow was continued for 54 hours during which time 215 g of the silane were used. The flow was then stopped and the system was allowed to stand intact for 66 hours.

The flow of N$_2$-silane mixture was again started at 0.25 liters/minute. After 24 hours, the flow was stopped and the pipe was treated for 20 hours with N$_2$ at 1 psi bubbled through H$_2$O. This was followed by an additional 54 hours of N$_2$-silane mixture at 0.25 liter/minute. This last combined treatment time of 78 hours consumed 306 g of the bis(dimethylamino)methylsilane.

It was now observed that the original massive leak in the pipe had been reduced to a slow leak. That is, a slight pressure (~2 psi) could be built up in the pipe and it required several seconds to leak out. The sand was removed so that the jute joint could be inspected. A tough polymer had formed completely around the joint, and, as the leak test indicated, it was estimated to be more than 90% sealed at 10 psi.

While the above examples were all carried out using bis(dimethylamino)methylsilane, it is clear that similar results will be obtained by the use of other aminosilanes within the ambit of the present invention and blends thereof. Indeed, appropriate blends, such as a mixture of bis(dimethylamino)dimethylsilane in combination with tris(dimethylamino)methylsilane results in a polymer on cohydrolysis which is similar to that obtained with room temperature vulcanizing silicone rubber. The sand or earth at the situs of the pipe leak acts as a weak reinforcing filler to give added strength. Even though the tris-compound noted above has a higher boiling point, i.e. a lower vapor pressure, than desired, when used in only small percentages of 1-5% of the silane blend, its partial pressure in the gas mixture makes it just as volatile as the bis(dimethylamino)dimethylsilane.

The instant invention has a number of advantages over the use of materials previously suggested. The end product is better, more flexible and more homogeneous; the starting compounds are safer, more stable and non-pyrophoric. No catalysts or gaseous organometallic compounds are necessary. The readily volatilizable compounds utilized form a leak sealing polymer under the proposed use conditions upon reaction with water or sand to form a self-sealing polysiloxane.

It will be obvious to those skilled in the art that various changes may be made without departing from the scope of the invention and the invention is not to be considered limited to what is described in the specification.

What is claimed is:

1. A method of forming a seal at the situs of a leak located in a vessel by polymerizing an organic monomer at said situs, comprising introducing a sealant consisting essentially of an aminosilane monomer into the interior of said vessel, said aminosilane monomer being readily volatilizable at the ambient temperature of said vessel and having the formula:

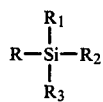

wherein R is H, halogen or R', and R' is alkyl of 1-4 carbons;
$R_1$ is halogen, R', —OR, —NHR' or —N(R')$_2$;
$R_2$ is halogen, R', —OR, —NHR' or —N(R')$_2$; and
$R_3$ is —NHR' or —N(R')$_2$;
said aminosilane monomer being introduced to said vessel under sufficient pressure and for a sufficient period of time to effect contact of said leak situs with said monomer in the vapor state and to effect polymerization of said monomer at said leak situs and sealing of the leak.

2. A method in accordance with claim 1, comprising, as a preliminary step, flushing said vessel with a moisture laden gas inert to said aminosilane.

3. A method in accordance with claim 1, wherein said vessel is a pipe buried in sand.

4. A method in accordance with claim 1, wherein said vessel is a pipe buried in moist earth.

5. A method in accordance with claim 1, wherein said aminosilane is bis(dimethylamino)methylsilane.

6. A method in accordance with claim 1, wherein said aminosilane is selected from the group consisting of bis(dimethylamino)dimethylsilane; methoxy-dimethylamino-methylsilane; methoxy-bis(dimethylamino)-methylsilane; dimethoxy-dimethylamino-methylsilane; and methoxy-dimethylamino-dimethylsilane.

7. A method in accordance with claim 1, wherein said aminosilane is a mixture of 1-5% tris-(dimethylamino)-methylsilane with the remainder being bis-(dimethylamino)dimethylsilane.

8. A method in accordance with claim 1, wherein said silane is carried in a gas inert thereto.

9. A method in accordance with claim 8 wherein said aminosilane is introduced into said vessel in a continuous manner at such a rate that the concentration of the monomer vapor does not exceed 25,000 ppm.

10. A method in accordance with claim 1, carried out at a temperature of 30° F. to 90° F.

11. A method in accordance with claim 1, wherein $R_1$ is R' or —OR'; and $R_2$ is —OR' or —N(R')$_2$.

12. A method in accordance with claim 1 wherein said vessel is a natural or fuel gas pipe, and said aminosilane is introduced, into natural or fuel gas continuously carried by said gas pipe, in an intermittent manner.

13. A sealed vessel obtained by the method of claim 1.

14. A sealed vessel obtained by the method of claim 9.

* * * * *

UNITED STATES PATENT AND TRADEMARK OFFICE
CERTIFICATE OF CORRECTION

PATENT NO. : 4,237,172

DATED : December 2, 1980

INVENTOR(S) : Joseph J. PACKO et al

It is certified that error appears in the above-identified patent and that said Letters Patent are hereby corrected as shown below:

Claim 1, line 11, change "-OR," to -- -OR',-- line 12, change "-OR," to -- -OR',--

Signed and Sealed this

Twenty-second Day of December 1981

[SEAL]

Attest:

Attesting Officer

GERALD J. MOSSINGHOFF

Commissioner of Patents and Trademarks